US00PP08034P

United States Patent [19]

Zaiger et al.

[11] Patent Number: Plant 8,034

[45] Date of Patent: Nov. 17, 1992

[54] PEACH TREE "SUGAR MAY"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 699,463

[22] Filed: May 13, 1991

[51] Int. Cl.[5] ..... A01H 5/00

[52] U.S. Cl. ..... Plt./42.1

[58] Field of Search ..... Plt./42

*Primary Examiner*—James R. Feyrer

[57] ABSTRACT

A new variety of peach tree with the following unique combination of features that are outstanding in a new variety:

1. Early maturity of large, white flesh fruit.
2. The regular and heavy production of fruit.
3. Vigorous upright growth.
4. Fruit with good flavor and eating quality.
5. Fruit with firm flesh, good handling and shipping qualities.
6. Fruit with attractive red skin color.

1 Drawing Sheet

ORIGIN OF THE VARIETY

The present new variety of peach tree was originated by us in our experimental orchard located near Modesto, Calif., and was selected as a first generation cross between two selected seedlings with the identification numbers of 29G560 and 54G262. The maternal parent 29G560 originated from a cross between O'Henry Peach (U.S. Plant Pat. No. 2,964) and Giant Babcock Peach (U.S. Plant Pat. No. 1,353) and the paternal parent 54G262 originated from a cross between Redwing Peach (U.S. Plant Pat. No. 621) and a selection of an early ripening, highly red colored nectarine of unknown parentage. A large group of seedlings from this first generation cross were grown and maintained under close observation by us and the present variety which evidenced distinctive desirable fruit characteristics was selected for asexual reproduction and commercialization.

ASEXUAL REPRODUCTION OF THE VARIETY

The present new variety of peach tree was asexually reproduced by budding, as performed by us in our experimental orchard located near Modesto, Calif., and shows that all said characteristics run true to form and are established and transmitted in succeeding propagations.

SUMMARY OF THE VARIETY

The new and distinct variety of peach tree is of large size, vigorous upright growth and a regular and productive bearer of large, firm, white flesh, clingstone fruit with good eating quality and the ability to ship to long distance markets. The fruit of the new variety is further characterized in comparison to Redwing Peach (U.S. Plant Pat. No. 621) by having firmer flesh, greater shipping quality, a higher degree of attractive red skin color and maturing approximately 14 days earlier.

BRIEF DESCRIPTION OF THE PHOTOGRAPHS

The accompanying color photographic illustrations show typical specimens of the foliage and fruit of the new variety of peach tree with the upper and lower surface of the leaves being shown as well as the exterior and sectional view of the fruit showing flesh coloration with a stone remaining in place. The photographs were taken shortly after the fruit was picked at maturity (firm ripe) and the colors are as nearly true as is reasonably possible in a color representation of this type.

DESCRIPTION OF THE VARIETY

The following is a detailed botanical description of the new peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium.
- *Shape.*—Usually pruned to vase shape.
- *Productivity.*—Productive.
- *Bearer.*—Regular.

Trunk:
- *Size.*—Medium stocky.
- *Texture.*—Medium shaggy.
- *Color.*—Brown to grayish brown (5-E-4) to (5-E-6).

Branches:
- *Size.*—Medium.
- *Texture.*—Smooth to medium rough.
- *Lenticels.*—Medium size. Numerous.
- *Color.*—Reddish brown to brown (8-E-7) to (8-E-5).

Leaves:
- *Size.*—Large. Average length — 6¾". Average width — 1½".
- *Form.*—Lanceolate. Pointed.
- *Margin.*—Crenate.
- *Thickness.*—Medium.
- *Texture.*—Smooth.
- *Petiole.*—Medium length. Medium thickness.
- *Glands.*—Reniform. Number varies from 1 to 5. Average number 2. Size — medium.
- *Color.*—Upper surface — green to deep green (27-F-6) to (27-F-8). Lower surface — light green to grayish green (27-E-4) to (27-E-6).

Flower buds:

*Size.*—Large.
*Form.*—Plump.
*Pubescence.*—Pubescent.

Flowers:
*Size.*—Large — showy.
*Blooming period.*—Mar. 1, 1990 to Mar. 7, 1990. Varies slightly with climatic conditions.
*Pollen.*—Present — self fertile.
*Color.*—Pink.

Fruit:
*Maturity when described.*—Firm ripe.
*Date of first picking.*—Jun. 3, 1990.
*Date of last picking.*—Jun. 10, 1990.
*Size.*—Large. Average diameter axially — $2\frac{3}{4}''$. Average transversely in suture plane — $2\frac{3}{4}''$.
*Form.*—Nearly globose — slightly larger on one side.
*Suture.*—Shallow — extends from base to apex.
*Ventral surface.*—Nearly round, very slightly lipped.
*Cavity.*—Rounded — slightly elongated in suture plane. Average depth — $\frac{1}{2}''$. Average breadth — $\frac{3}{4}''$.
*Base.*—Retuse.
*Apex.*—Short — varies from slight pistil point to slightly retuse.

Skin:
*Thickness.*—Medium.
*Texture.*—Medium — tenacious to flesh.
*Tendency to crack.*—None.
*Down.*—Moderate amount. Short in length.
*Color.*—Yellow ground color (5-A-5) to (5-A-6) overspread with red (9-C-7) to (9-D-8).

Flesh:
*Ripens.*—Evenly.
*Texture.*—Firm.
*Fibers.*—Few and tender.
*Juice.*—Moderate.
*Aroma.*—Moderate.
*Amygdalin.*—Undetected.
*Flavor.*—Good, mild, good balance between sugar and acid.

*Eating quality.*—Good.
*Color.*—White to greenish white (26-A-1) to (26-A-2). Pit cavity greenish white (26-A-3) to (26-A-4). Slight bleeding of pale red (9-A-3) to (9-A-4) just above apex of stone.

Stone:
*Type.*—Clingstone.
*Size.*—Large. Average length — $1\frac{1}{2}''$. Average width — $1''$. Average thickness — $\frac{5}{8}''$.
*Form.*—Oval.
*Base.*—Mostly rounded, some straight.
*Apex.*—Acuminate. Large size.
*Sides.*—Mostly equal — varies from equal to unequal.
*Surface.*—Irregularly furrowed toward apex, pitted toward base.
*Ridges.*—Rounded.
*Tendency to split.*—Very slight.
*Color.*—Light brown to brown (6-C-5) to (6-D-5).

Use: Dessert.
*Market.*—Local and long distance.
Keeping quality: Good.
Shipping quality: Good.

The peach tree, its flowers and fruit herein described may vary in slight detail due to climatic, soil and cultural practices under which the variety may be grown. The present description is that of the new variety grown under the ecological conditions prevailing near Modesto, Calif.

We claim:

1. A new and distinct variety of peach tree, substantially as illustrated and described, which is of large size, vigorous upright growth and a productive and regular bearer of large, early maturing, white flesh, clingstone fruit with good eating and shipping qualities; the fruit is further characterized in comparison to the white flesh variety Redwing Peach (U.S. Plant Pat. No. 621) by having firmer flesh, greater shipping quality, a higher degree of attractive red skin color and maturing approximately 14 days earlier.

* * * * *

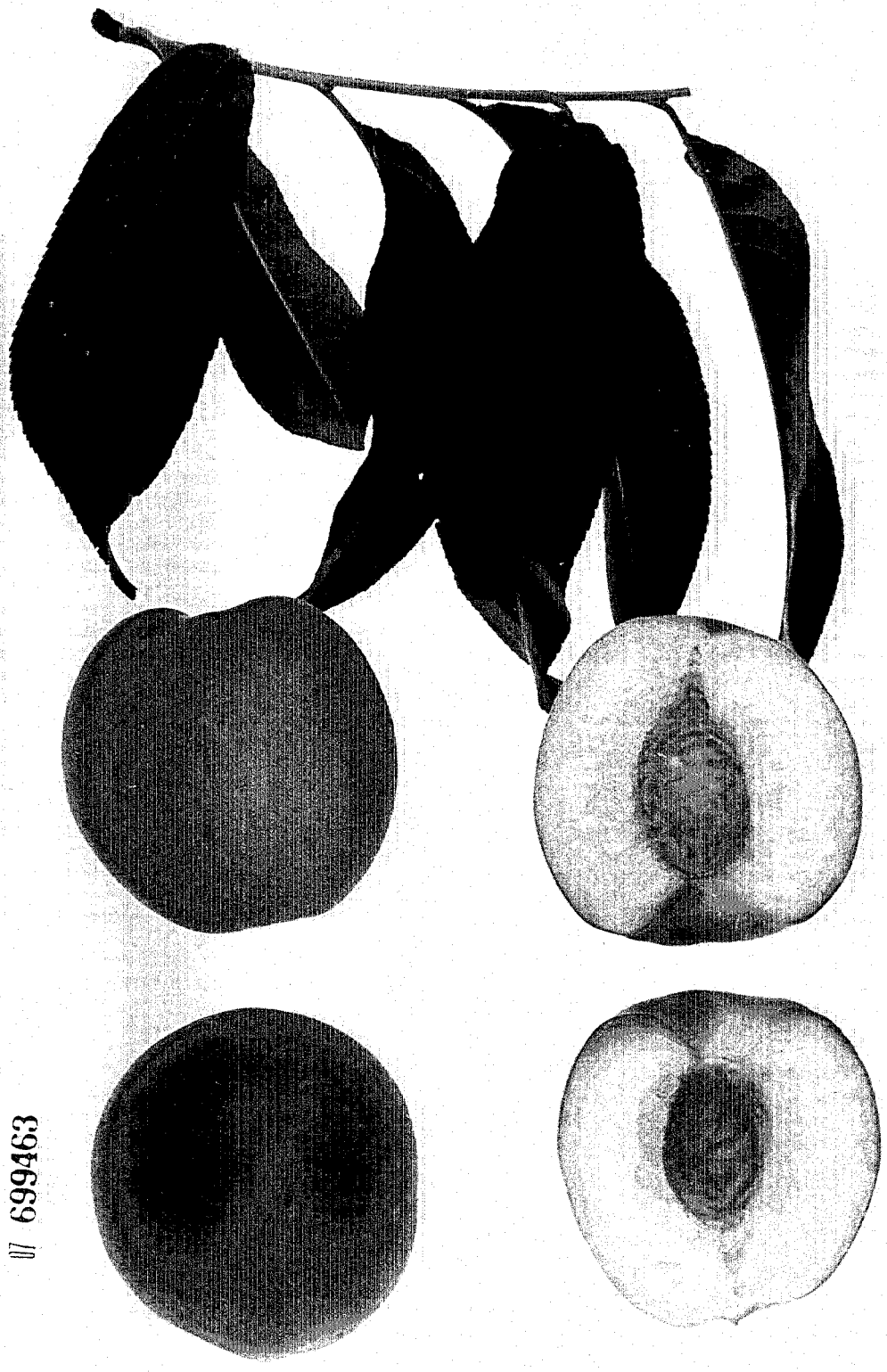
07 699463